United States Patent [19]
Frazee

[11] 3,951,260
[45] Apr. 20, 1976

[54] SURVIVAL KIT

[76] Inventor: Kenneth G. Frazee, 1193 Mojave, Idaho Falls, Idaho 83401

[22] Filed: Nov. 25, 1974

[21] Appl. No.: 527,169

[52] U.S. Cl. ............................. 206/223; 206/803; 116/124 B; 116/DIG. 9
[51] Int. Cl.² ...................................... B65D 79/00
[58] Field of Search ........... 206/229, 803, 223, 102; 116/DIG. 9, 124 B; 343/706

[56] References Cited
UNITED STATES PATENTS

| | | | |
|---|---|---|---|
| 2,062,973 | 12/1936 | Gluckstein | 206/223 |
| 2,448,171 | 8/1948 | Campbell | 206/803 |
| 2,826,297 | 3/1958 | Hein, Jr. | 206/223 |
| 3,002,490 | 10/1961 | Murray | 116/DIG. 9 |
| 3,049,227 | 8/1962 | Reinemer | 206/102 |
| 3,387,698 | 6/1968 | Hendricks et al. | 206/223 |
| 3,727,229 | 4/1973 | Clinger et al. | 343/706 |

Primary Examiner—William T. Dixson, Jr.
Attorney, Agent, or Firm—Clarence A. O'Brien; Harvey B. Jacobson

[57] ABSTRACT

An open top housing is provided including upstanding peripheral side walls joined at their lower marginal portions by a bottom wall extending therebetween and further including a removable top wall provided with depending peripheral flanges telescoped over at least the upper marginal portions of the side walls of the housing with the top wall closing the open top of the housing in a fluid-tight manner. Coacting latch structure is carried by exterior portions of corresponding side walls and flanges of the housing and top wall for removably securing the top wall in the closed position and the interior of the housing includes baffles dividing the housing into separate compartments. One of the compartments includes a pressurized container of lighter-than-air gas and a second compartment includes a collapsible inflatable balloon which may be inflated by the aforementioned gas. Further, a winding member is journaled from the inner surface of the top wall and has a length of flexible tether line wound thereon attachable to the balloon, the latter being reasonably large when inflated and of a color which is readily viewable from a distance.

3 Claims, 4 Drawing Figures

U.S. Patent April 20, 1976 3,951,260
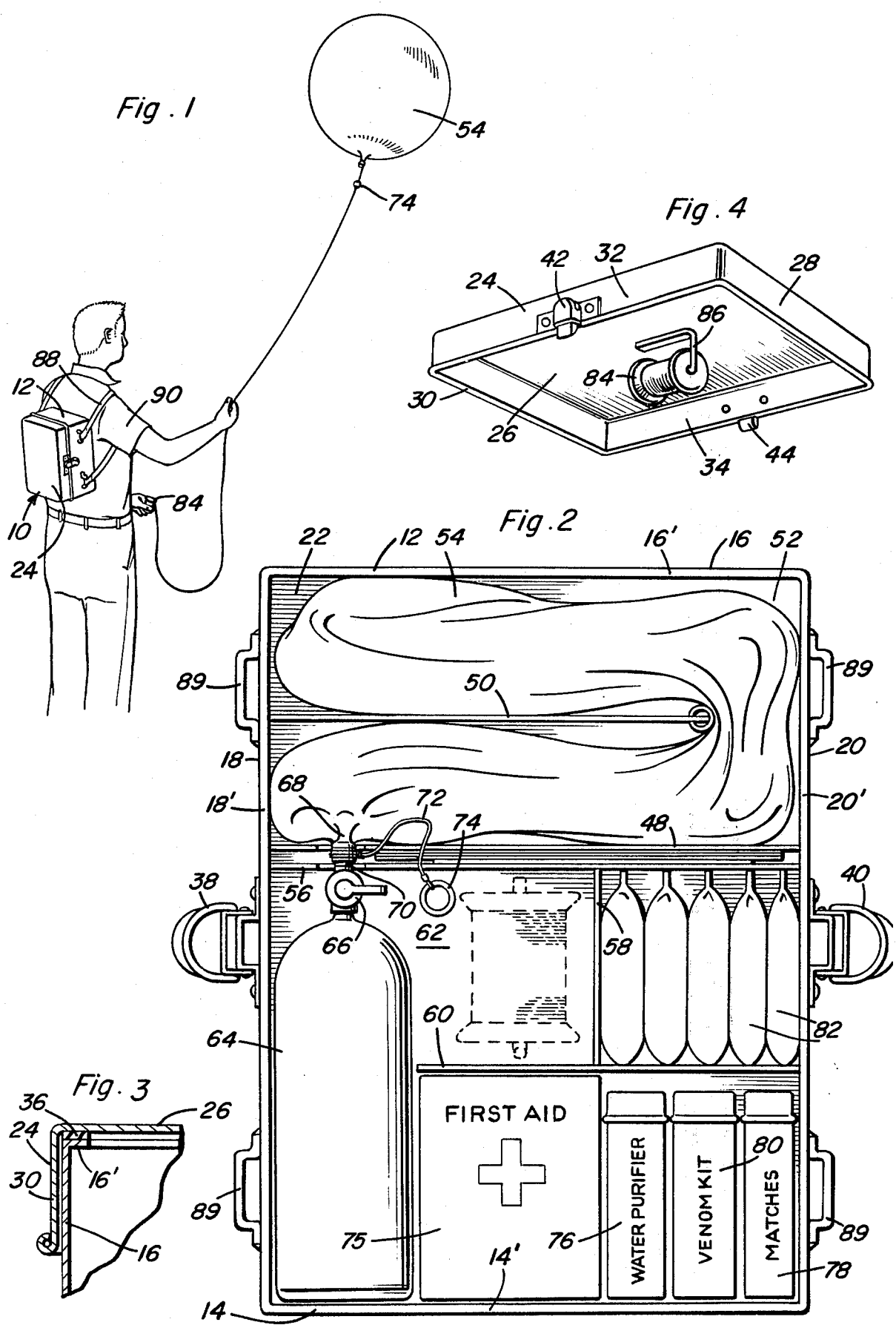

SURVIVAL KIT

BACKGROUND OF THE INVENTION

Heretofore various different types of survival kits have been designed for use by persons traveling great distances by water, air and foot and some of these prior survival kits have included first aid kits and inflatable signal balloons. However, most previously known survival kits have for one reason or another not been wholly satisfactory in substantially all environments which may be encountered in open spaces.

Examples of previously patented survival kits including some of the structure of the instant invention are disclosed in U.S. Pat. Nos. 2,395,006, 2,619,303, 2,629,115 and 2,646,019.

SUMMARY OF THE INVENTION

The survival kit of the instant invention has been designed to provide a readily transportable structure including a water-tight housing in which a large inflatable signal balloon, a supply of lighter-than-air gas under pressure and a tether line are stored. The housing further includes compartments for additionally storing food concentrates, a first aid kit, matches, a water purification kit and a venom kit. Still further, the housing includes a removable cover which may be securely fastened in the closed position for maintaining the housing water-tight whenever access thereto is not desired and the cover of the housing acts as a support for a journaled spool or winding member upon which a tether line for the aforementioned balloon is rotatably supported.

The main object of this invention is to provide a survival kit including the necessary components and structure thereof enabling the kit to be substantially wholly effective for supporting survival of persons in open spaces.

Another object of this invention, in accordance with the immediately preceding object, is to provide a survival kit constructed in a manner whereby it is maintained waterproof until access to the interior thereof is desired and which may be reclosed at any subsequent time in a manner to re-establish its waterproofness.

Another important object of this invention is to provide a survival kit including food concentrates and a water purifying kit as well as a first aid kit so as to meet at least the basic food, water and medical treatment requirements of an attendant individual.

A still further object of this invention is to provide a survival kit additionally including a supply of matches and a venom kit for use in the event it is necessary to start a fire or to treat a venomous bite.

Still another important object of this invention is to provide a survival kit of reasonably small dimensions and yet which will be effective in enabling the attendant person to erect a signal detectable for many miles.

A final object of this invention to be specifically enumerated herein is to provide a survival kit in accordance with the preceding objects and which will conform to conventional forms of manufacture, be of simple construction and easy to use so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of a person having the housing of the survival kit supported from his shoulder by means of a shoulder strap attached to the housing and with the inflatable signal balloon of the survival kit in a partially raised condition;

FIG. 2 is a top plan view of the survival kit with the top cover thereof removed;

FIG. 3 is a fragmentary vertical sectional view illustrating the manner in which the top cover of the housing is sealed relative to the latter against the entrance of moisture into the interior of the kit; and FIG. 4 is a perspective view of the removable cover for the housing portion of the kit illustrating the manner in which the winding member or spool for the tether line to be attached to the inflatable balloon is supported from the underside of the top wall of the cover.

DETAILED DESCRIPTION OF THE INVENTION

Referring now more specifically to the drawings, the numeral 10 generally designates the survival kit of the instant invention. The kit 10 includes an open top housing 12 having upstanding opposite end walls 14 and 16 as well as opposite side walls 18 and 20 interconnected by means of a bottom wall 22 extending between the lower marginal edges of the walls 14, 16, 18 and 20.

The kit 10 further includes a cover 24 for the housing 12 and the cover 24 includes a top wall 26 and integral depending opposite end flanges 28 and 30 as well as opposite side depending flanges 32 and 34.

The upper marginal portions of the walls 14, 16, 18 and 20 terminate in inwardly directed horizontal flange portions 14', 16', 18' and 20', respectively, and the upper surfaces of these flanges have a seal strip 36 secured thereover.

With attention now invited more specifically to FIG. 3 it may be seen that the cover 24 may be removably telescoped downwardly over the open top of the housing 12 with the flanges 28, 30, 32 and 34 telescoped downwardly over the side walls 14, 16, 18 and 20 and the outer peripheral portions of the undersurface of the top wall 26 sealingly engaged with the seal strip 36.

The outer surfaces of the mid-portions of the side walls 18 and 20 include over-center bail type latches 38 and 40 releasably engageable with coacting keepers 42 and 44 carried by the flanges 32 and 34. The latches 38 and 40 are operative to retain the cover 24 in a tightly closed condition over the open top of the housing 12 in tight sealed engagement with the seal strip 36.

The interior of the housing 12 includes partitions 48 and 50 defining a tortuous compartment 52 in which to receive a large diameter deflated balloon 54 and additional partitions 56, 58 and 60 define a compartment 62 in which to receive a pressurized container 64 of a gas lighter than air. The container 64 includes a valved outlet assembly 66 and the balloon 54 includes an inlet neck 68 equipped with a check valve assembly 70 removably engaged with the valved outlet assembly 66 and having one end of a short hand line secured thereabout. The other end of the hand line 72 includes an anchor ring 74 for a purpose to be hereinafter more fully set forth.

The interior of the housing 12 further includes a first aid kit 75, a water purification kit 76, a container of matches 78 and a snake bite kit 80 in addition to containers 82 of food concentrates. Still further, the compartment 62 includes an unoccupied area to the immediate left of the partition 58 as viewed in FIG. 2 of the drawings into which a spool 84 rotatably supported from a mount 86 anchored to the inner surface of the top wall 26 is receivable when the cover 24 is in the closed position. The spool 84 has one end of a tether line anchored thereto and the line is wound about the spool 84 with the free end thereof readily attachable to the ring 74.

In operation, a back strap 88 is attached to suitable anchors 89 carried by the side walls 18 and 20 and may be utilized to support the housing 12 and its cover 24 from a person 90.

The back strap may thus be used to carry the survival kit 10 in a convenient manner should the person desire to walk toward a location in which he believes help may be available.

If the person 90 finds it necessary to erect a visual signal, he may remove the cover 24 of the housing 12 and inflate the balloon 54 after having attached the tether line on the spool 84 to the ring 74. Then, after the balloon 54 has been inflated the valve assembly 70 may be disengaged from the valved outlet assembly 66 and the line on the spool 84 may be allowed to unwind so as to enable the inflated balloon 54 to rise to a considerable height. It is to be understood that the balloon 54 will be of considerable size when inflated and that it will be of a color to be visible for at least several miles.

After the balloon 54 has been raised, the tether line 84 may be securely fastened to the person 90 or to any anchoring means and the cover 24 may be re-applied over the open top of the housing 12 and secured in the closed position to maintain the interior of the housing sealed against water from the exterior thereof. At any time access to the interior of the housing 12 is desired it is merely necessary to temporarily remove the cover 24 and to then re-secure the cover 24 in a closed position.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A survival kit including an open top housing provided with upstanding peripheral side walls joined at their lower marginal portions by a bottom wall extending therebetween and further including a removable top wall provided with depending peripheral flanges telescoped over at least the upper marginal portions of said upstanding side walls with said top wall sealingly engaged with the open top of said housing rendering the latter waterproof, coacting releasable latch means carried by the exterior portions of corresponding flanges and side walls releasably securing said top wall in the closed position, said housing including interior baffle means dividing the interior of said housing into separate article receiving compartments, one of said compartments including gas supply means for discharging a gas lighter than air and a second of said compartments including a collapsed inflatable balloon therein capable of operative association with said gas supply means for inflating the balloon, and a winding member journaled from a central portion of the inner surface of said top wall having a length of flexible tether line wound thereon attachable to said balloon, when inflated, to tether said ballon to said top wall when the latter is removed from said housing and placed in inverted position upon a suitable support surface, said winding member occupying only a small portion of the plan area of said top wall, whereby the unoccupied areas of said top wall may be weighted with suitable weights, such as rocks, when the top wall is inverted, said one compartment including a portion thereof not occupied by said gas supply means and in which said winding member is received when said top wall is secured over said housing.

2. The combination of claim 1 wherein said gas supply means includes a pressurized container including a valved outlet, said balloon including an inlet neck removably engageable with said outlet for inflating said balloon upon the opening of the valve portion of said outlet, and said inlet neck including a check valve operative to freely admit gas into said balloon and to prevent the flow of gas from within said balloon outwardly through said neck.

3. The combination of claim 1 wherein said second compartment comprises an elongated compartment including an upstanding central longitudinal partition extending from one end of said compartment and terminating a spaced distance from the other end of said compartment, said balloon being collapsed into an elongated flexible member with its opposite ends disposed in said one end of said compartment on opposite sides of said partition and the central portion of said flexible member passed around the end of the partition spaced from the other end of said compartment.

* * * * *